United States Patent
Kemp et al.

(10) Patent No.: US 8,327,606 B2
(45) Date of Patent: Dec. 11, 2012

(54) METHOD AND APPARATUS FOR STERILIZATION

(75) Inventors: Terry Dean Kemp, Auckland (NZ);
Christo Andre De Klerk, Gold Coast (AU)

(73) Assignee: Mercer Technologies Limited, Auckland (NZ)

(*) Notice: Subject to any disclaimer, the term of this patent is extended or adjusted under 35 U.S.C. 154(b) by 203 days.

(21) Appl. No.: 12/083,812

(22) PCT Filed: Oct. 20, 2006

(86) PCT No.: PCT/NZ2006/000268
§ 371 (c)(1), (2), (4) Date: Apr. 20, 2009

(87) PCT Pub. No.: WO2007/055595
PCT Pub. Date: May 18, 2007

(65) Prior Publication Data
US 2009/0217626 A1    Sep. 3, 2009

(30) Foreign Application Priority Data

Oct. 20, 2005 (NZ) ..................... 543085

(51) Int. Cl.
*B65B 31/06* (2006.01)
(52) U.S. Cl. .......... 53/86; 53/407; 53/408; 53/425; 53/510; 422/26; 422/33
(58) Field of Classification Search ............ 53/425, 53/79, 86, 510, 403, 407, 408, 469, 434; 422/33, 38, 302, 26
See application file for complete search history.

(56) References Cited

U.S. PATENT DOCUMENTS

| | | | |
|---|---|---|---|
| 3,396,839 A * | 8/1968 | Suel Grant et al. | 206/370 |
| 3,564,861 A * | 2/1971 | Andersen et al. | 62/48.1 |
| 3,630,665 A * | 12/1971 | Andersen et al. | 422/33 |
| 3,939,287 A | 2/1976 | Orwig et al. | |
| 4,221,101 A * | 9/1980 | Woods | 53/79 |
| 4,660,721 A | 4/1987 | Mykleby | |
| 4,798,292 A * | 1/1989 | Hauze | 206/439 |

(Continued)

FOREIGN PATENT DOCUMENTS
EP    0982236 B1    5/2003
(Continued)

OTHER PUBLICATIONS

Mercer Technologies Limited, PCT Search Report and Written Opinion dated Feb. 14, 2007, PCT/NZ2006/000268 filed Oct. 20, 2006, 9 pages.

*Primary Examiner* — Thanh Truong
(74) *Attorney, Agent, or Firm* — Blakely, Sokoloff, Taylor & Zafman LLP

(57) ABSTRACT

A method and apparatus for sterilization in which items to be sterilized are placed in an impervious sealable package and the sterilization process is carried out within the package. The apparatus (10) includes a cabinet (18) in which a package (P) preferably with a carrier (11) located within, can be positioned. A snorkel (17) is inserted into the package (P) and via connector (23) vacuum, pressure and sterilant can be applied to the interior of the package (P). A sealing arrangement (14b, 22b) can seal the package closed after the sterilization process has been completed.

13 Claims, 5 Drawing Sheets

U.S. PATENT DOCUMENTS

| | | | |
|---|---|---|---|
| 5,135,715 A * | 8/1992 | Andersen | 422/28 |
| 5,555,704 A * | 9/1996 | Caufield et al. | 53/425 |
| 5,561,964 A * | 10/1996 | McIntyre et al. | 53/75 |
| 5,779,973 A * | 7/1998 | Edwards et al. | 422/28 |
| 6,391,260 B1 * | 5/2002 | Davis et al. | 422/28 |
| 6,543,491 B1 * | 4/2003 | Chung | 141/65 |
| 6,622,457 B2 * | 9/2003 | Kurth | 53/425 |
| 7,021,485 B1 * | 4/2006 | Baker et al. | 220/326 |
| 2005/0084415 A1 * | 4/2005 | McVey et al. | 422/28 |
| 2005/0198923 A1 * | 9/2005 | Wolters et al. | 53/425 |

FOREIGN PATENT DOCUMENTS

| | | |
|---|---|---|
| FR | 2406567 | 5/1979 |
| WO | WO-8401507 | 4/1984 |
| WO | WO-9609210 | 3/1996 |
| WO | WO-02053194 | 7/2002 |

* cited by examiner

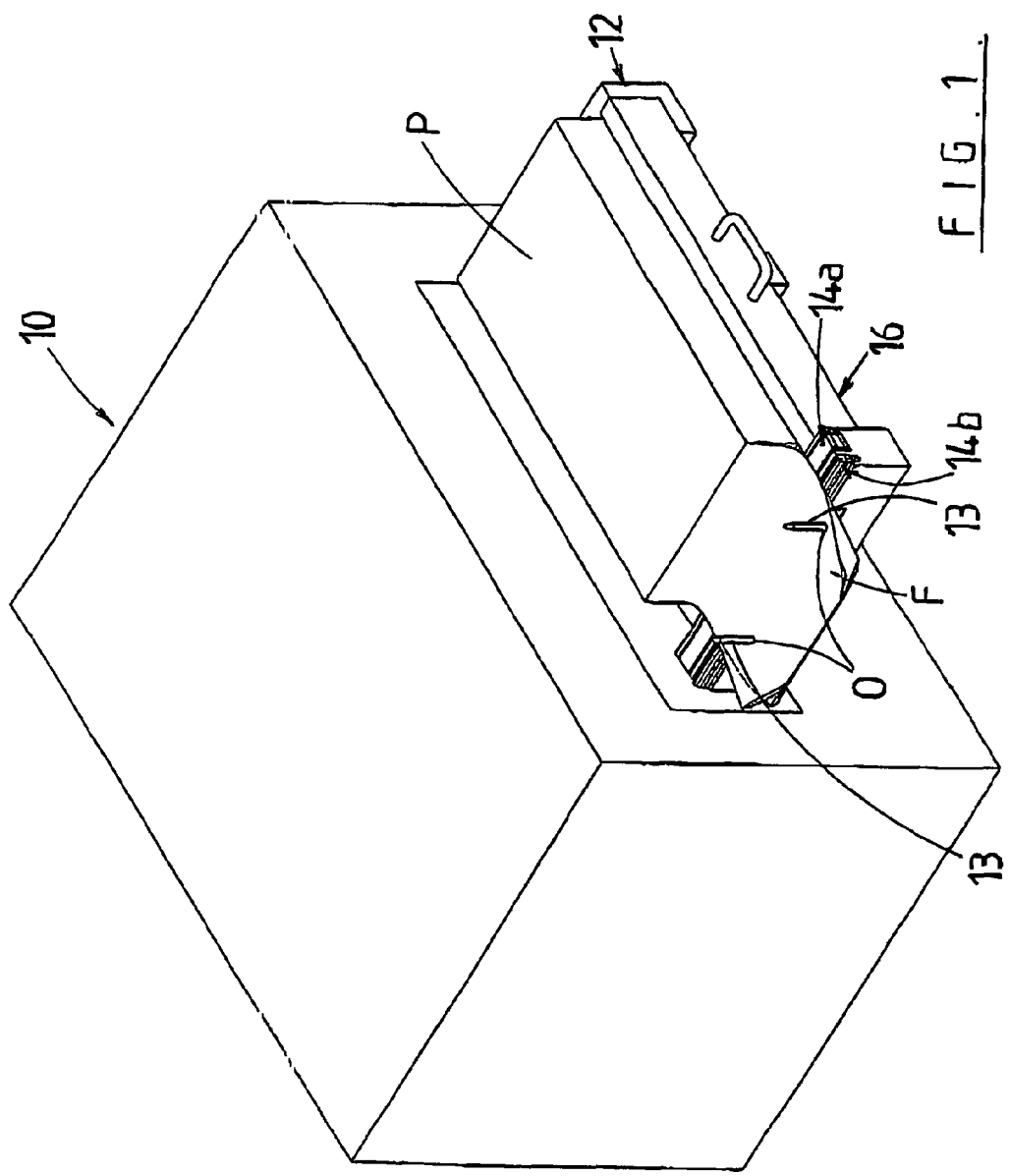

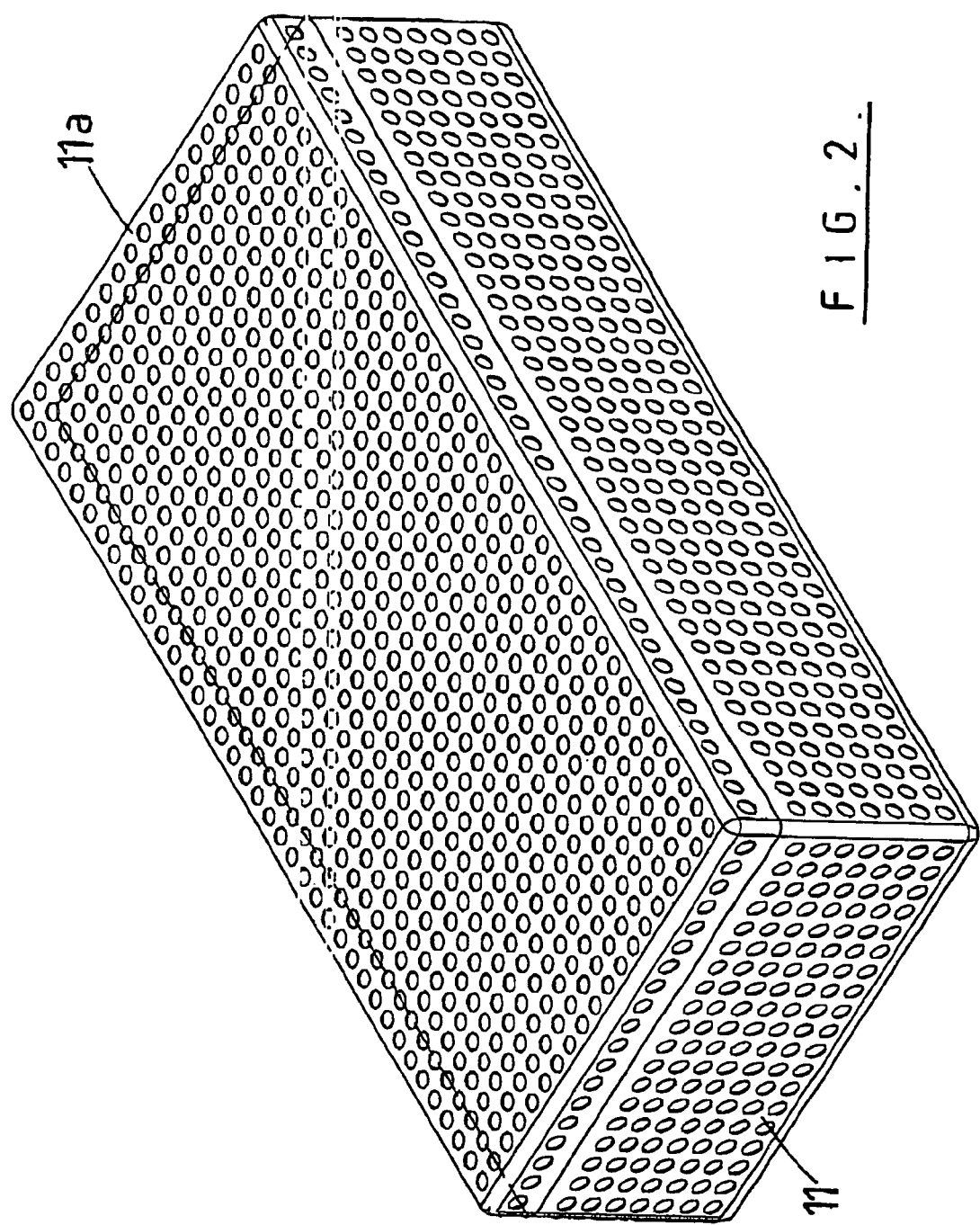

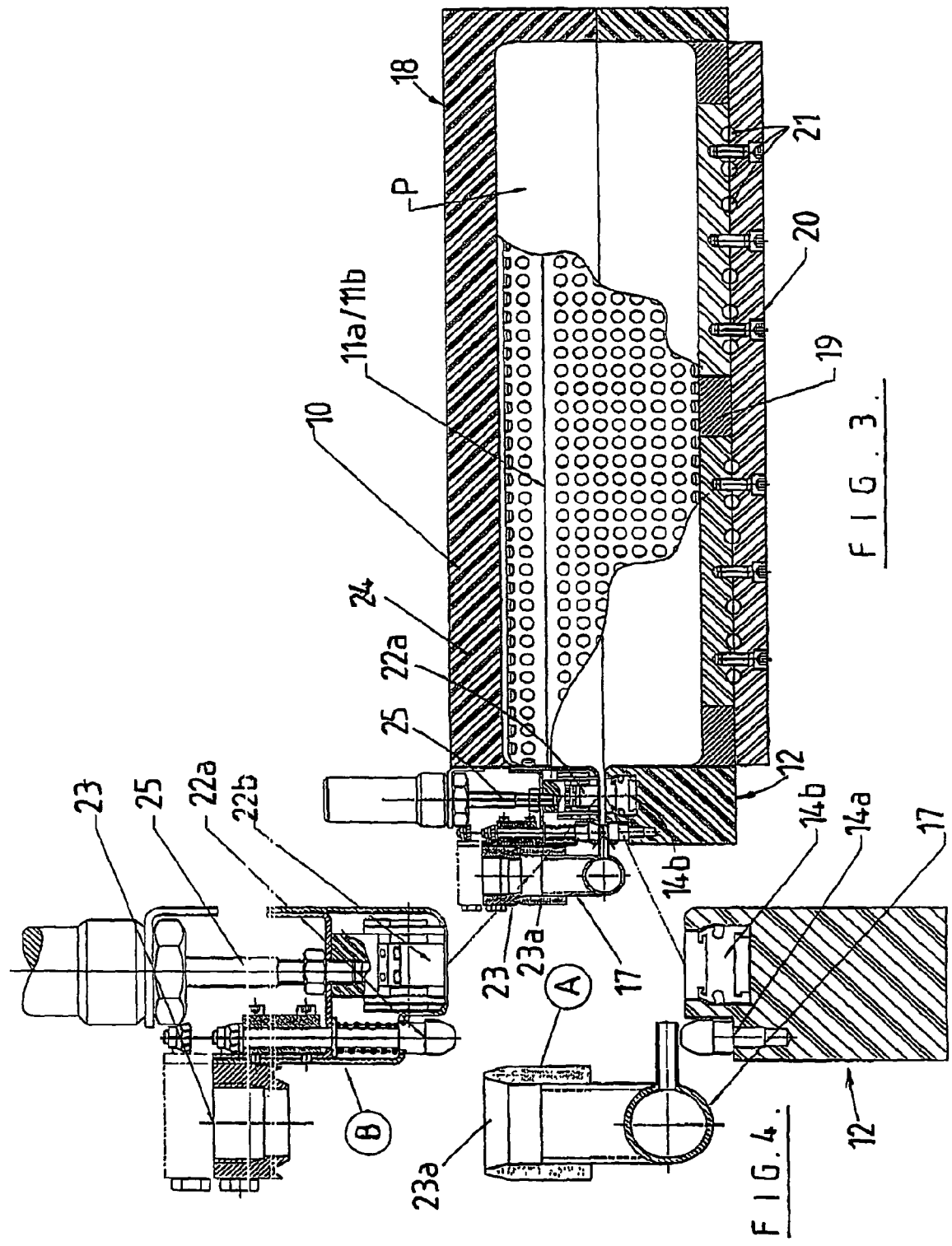

METHOD AND APPARATUS FOR STERILIZATION

BACKGROUND TO THE INVENTION

The present patent application is a Utility of Application No. PCT/NZ 2006/000268, filed Oct. 20, 2006.

This invention relates to a method and apparatus for sterilization. More particularly the invention relates to a method and apparatus for sterilization and vacuum packing without the requirement for a conventional pressure vessel or chamber.

Sterilization is an absolute necessity for various industries typically health care, laboratory, pharmaceutical and food processing industries. The most common and proven method used for sterilization is sterilization by pressurized high temperature steam in a pressure chamber or vessel for a prescribed period of time. Pressurized high temperature steam within a stainless steel pressure chamber is the preferred method for sterilization of laboratory equipment and in the industrial manufacturing sector.

It is necessary in hospital and health care environments, laboratory environments and in the pharmaceutical and food processing industry to either sterilize, autoclave, cook, pasteurize or retort various devices, instruments, material and/or products with pressurized high temperature steam or by means of a low temperature medium (e.g. ethylene oxide or equivalent low temperature sterilant) in a pressure vessel.

Various types of sterilization pressure vessels and autoclave chambers are historically utilized to sterilize such objects, items or products (hereinafter "items"). In all instances the sterilant must make contact with the surface of the or each item to be sterilized in order to enable sterilization to occur.

For moist heat sterilization using steam as the sterilant, it is essential that all surfaces of the items requiring sterilization are subjected to saturated steam at a predetermined temperature and pressure, for a predetermined period of time. Proper steam penetration requires adequate air removal.

In the medical environment, it is necessary that all medical items (equipment and materials) utilized for the treatment of patients are inherently safe for use so that the chance of spreading diseases is kept as low as possible. Hospital acquired infection is clearly the last thing either a patient or the hospital wants.

At the end of a correct sterilization process, items inside the sterilization chamber are sterile. The challenge to sterilizer manufacturers has been the variety of loads and varied manner of loading both in respect of how items are loaded and positioned in the chamber and how the load may be packaged. The load therefore has a direct impact on the relative efficacy of each method of removing air from the chamber and the load and is still a matter under debate.

The European standards (EN 13060 and EN 285—MDA SN 2001 [34]) have established several test methods that demonstrate the ability of a selected sterilization cycle to effectively remove air from hollow or cannulated devices and its ability to process porous items, such as packaged trays or drapes.

The problem therefore is that a sterilizer operator must make sure that the sterilizer and sterilization cycle selected for use is suitable for the intended purpose. Due to these complexities the EN 867 standard was introduced which describes specific non-biological indicator systems and process challenge devices for use in performance testing of sterilizers.

An unavoidable problem that faces sterilization practitioners is that the air in the room where the sterilizer is installed contains dust particles, which may carry micro-organisms. Accordingly, when the sterile load is taken out of the sterilizer, it may soon be contaminated again. Additionally sterile goods may be stored for quite some time before they are used. Moreover, they are transported through the hospital to the place they are to be used. It thus is obvious, that, when not protected, the items may most likely be re-contaminated by the time they are used.

Consequently the items must be put in packaging to prevent recontamination after sterilization. To minimize recontamination and augment the logistics and materials handling expediency of the sterilization process, the item(s) are usually prepackaged. The packaging heretofore typically include muslin wraps, various paper wraps and non-woven wraps, laminated film pouches and sterilization containers.

Sterile services technicians must have an understanding of how to properly select and apply the correct wrappers for the sterilization method chosen. The manufacturer and distributors must be able to provide detailed specifications regarding the properties of the product as well as documentation of acceptable results of its past performances. Improper selection of materials and packaging application can and will impede the sterilizing process.

Technicians are also responsible for quality assurance issues. They must assemble each package with care, being observant not to tear or damage the wrapper.

Each package is uniquely organized, depending upon content, to promote the sterilization process. Special attention must also be given to how the sterilizer is loaded.

When using the various types of wraps, medical instruments are placed in a tray, wrapped by a recommended procedure, taped, labelled and placed in a steam or low temperature sterilizer. During sterilization the packaging must allow air to be removed and steam or low temperature medium to penetrate the packaging and kill any bacteria. After sterilization the packaging must enable the condensate back out and should provide an effective microbial barrier for immediate use of the sterile items.

Disadvantages in the use of the sterilization wraps include the limited shelf life of the wrapped instruments, the porous nature of the wrap, the likelihood of retaining moisture, the fact that the wraps are not easily stackable and potential punctures of wrapping materials thereby causing contamination. In addition the wrapping of packs necessitates a certain skill set and requires a high labour content due to the multilayer barrier construction and requires specially trained staff to undertake the work.

It is essential that a packaging system with its content meet the requirements in terms of sterility maintenance and protection of its contents. That is why any packaging should be validated in combination with the actual load and the sterilization process used.

Various sterilization containers have been heretofore proposed which provide a hermetically sealed container with various filters which provide a relatively long shelf life, which cannot be easily punctured, which enable improved organization of the medical instruments and which are stackable. Sterilization containers made of metal such as stainless steel and aluminum are used, but are expensive. These devices are generally also opaque, thereby preventing a visual inventory of the container interiors.

Consequently, sterilization containers made of plastics have been developed. These are constructed to withstand the harsh environments of the sterilization chamber and are clear such that inventories of the containers can be seen through the container. The containers, however, are relatively expensive and still require to be put through the sterilization pressure chamber.

SUMMARY OF THE INVENTION

The novel concept forming the present invention is sterilization within a sealable packaging device (plastic bag/container or similar) which is vacuum sealed (preferably automatically) at the end of the sterilization process. The combination of an innovative apparatus and sealable packaging device in effect replaces the necessity for the sterilization pressure chamber.

We have thus devised a method of introducing a sterilant (typically steam) and vacuum into a packaging/package (plastic bag) in order to sterilize the contents. Because the pressure is contained within the package and apparatus there is no need for an expensive pressure vessel. Furthermore the sterilant is only introduced into the package, not a large chamber containing the items to be sterilized. As a result the services (steam/vacuum) requirements are significantly reduced thereby offering increased processing efficiencies.

The process we have invented removes the issues identified above in relation to wraps because the sterilization occurs within the package and the packaging is non-porous. In fact because we vacuum seal the sterile items within the impervious packaging at the end of the sterilization process the possibility of recontamination is completely eliminated.

We believe that the process we have invented overcomes most shortcomings of current procedures whereby from the moment the item is placed in the sealable packaging (plastic bag) before sterilization, it remains within the packaging during the sterilization cycle, is sealed within the sterile packaging after completion of the sterilization cycle and remains safely in the sealed impervious packaging until the moment it is opened, just before use.

According to one broad aspect of the invention there is provided a method of sterilization including the steps of placing the item(s) to be sterilized into an impenetrable sealable packaging, carrying out a sterilization process by applying a vacuum to the interior of the sealable packaging and introducing sterilant, and sealing the sealable packaging at the completion of the sterilization process.

Preferably the sealable packaging is vacuum sealed at the completion of the sterilization process.

In the preferred form of the invention the item(s) to be sterilized are placed in a carrier which is in turn placed in the sealable packaging prior to the sterilization process. The carrier will be of perforated form.

According to a second broad aspect of the invention there is provided sterilization apparatus including means to locate and retain an impenetrable sealable package containing a carrier with item(s) to be sterilized, snorkel means engageable in an open mouth of the package and means to seal the open mouth about the snorkel means, means to selectively apply vacuum and sterilant to the interior of the package to carry out a sterilization process therein and sealing means to seal the open mouth of the package at the conclusion of the sterilization process.

A further embodiment may be that the apparatus incorporates a bag forming device that may construct the bag from a laminate film in sheet or roll form.

BRIEF DESCRIPTION OF THE DRAWINGS

In the following more detailed description of the invention according to a preferred embodiment reference will be made to the accompanying drawings in which:—

FIG. 1 is a perspective illustration of the apparatus of the invention with packaging containing an item or items to be sterilized, the packaging being shown in place on an drawer arrangement, FIG. 2 is a perspective view of a reusable autoclavable cage or tray with lid to be invested into the packaging, FIG. 3 is a cross-sectional elevation view of the cage or tray with lid inside the packaging and within the apparatus with a clamping and sealing mechanism shown in a working position with the packaging clamped about the snorkel, FIG. 4 is a more detailed view of the snorkel, clamping and sealing mechanism and services socket arrangement, but with the clamping and sealing mechanism shown in the rest position.

DETAILED DESCRIPTION OF A PREFERRED EMBODIMENT OF THE INVENTION

Figure 5:
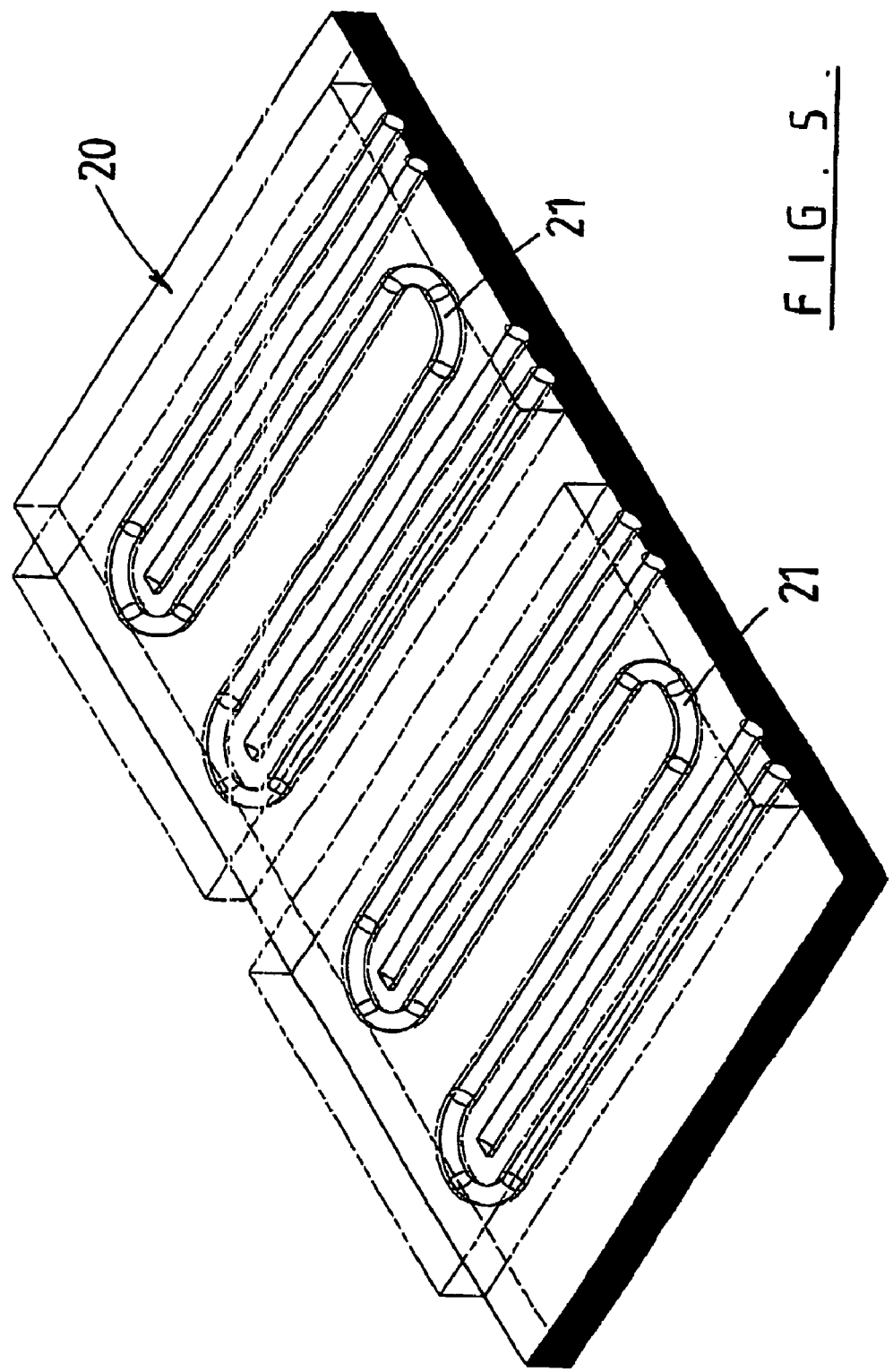
FIG. 5 is a perspective view of an electrically heated steam generating element of the apparatus.
Figure 6:
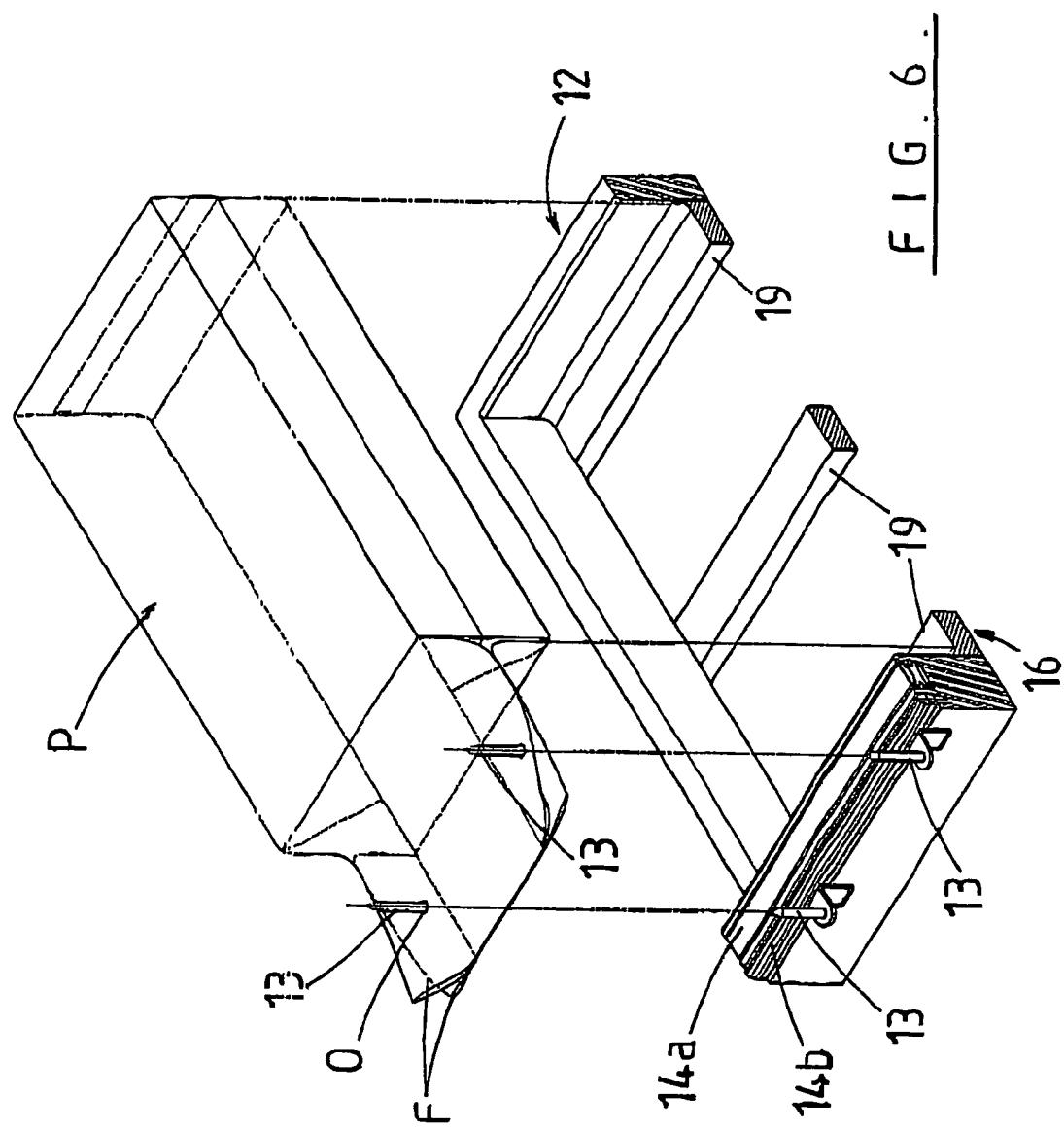
FIG. 6 is an exploded perspective view of the packaging and the drawer, part of which has been removed in the interests of clarity.

From the following description it will be evident that the requirements listed below are necessary:

Enabling sterilization. The packaging will allow air that is in the packaging to be driven out and the sterilant or sterilizing agent to reach all surfaces of its content (items).

Compatible with the sterilization process. The combination of the apparatus and packaging will be able to withstand the conditions that occur during the sterilization process such as pressure changes, high temperature and humidity.

Maintaining Sterility. After taking the sealed and optionally vacuum packed sterile item(s) out of the apparatus it/they will remain sterile during handling, transportation and storage until use.

Strong. The packaging will remain intact after any handling, storage and shipping.

Ensure product integrity and patient safety. The packaging/sterilization process will not affect the item(s) in any other way, which may affect the quality of the item(s) or which might endanger the patient or process on which the sterile item(s) will be used.

Preferably the packaging will also provide or facilitate in the following:—

Indicator. The packaging will be able to bear a clearly visible marking indicating whether or not the item is sterilized and with an option to bar code or label the packaging.

Facilitate aseptic opening and presentation. When opening a sealed packed sterile item(s), the packaging will facilitate aseptic opening and presentation. This implies:

simple opening when taking out sterile items from the packaging, it will not be possible to touch the un-sterile outer side of the packaging, the design incorporates an autoclavable perforated cage or tray with lid (preferably homopolymer polypropylene or similar) that the items are placed in prior to insertion into the packaging (plastic bag).

Visible that it was opened. Opening will result in a clearly visible indication that the packaging has been opened.

It is anticipated that the method of sterilization according to the invention will provide substantial efficiencies in the sterilization process model. Traditional sterilization cycles require up to 20 minutes of air-removal from the chamber and packages prior to sterilant introduction, (for steam typically 3-4 minutes @ 134 degrees Celsius of steam penetration for sterilization) and then 20-40 minutes of vacuum drying to remove the condensate from the chamber and packages.

The process of the present invention will remove air from inside the packaging within seconds/minutes (typically less than 5 minutes), sterilization time to international recognized standards and then remove the majority of the condensate within minutes (typically less than 5 minutes). It is envisaged that most sterilization cycle time(s) may be reduced by more than 50%.

The sterilized load (items) will be sealed (possibly vacuum sealed) in the packaging at the end of the sterilization cycle and there will be no requirement for the load to be completely dry as the packaging will be non-porous. Nevertheless it is believed that the invention will result in less likelihood of wet load problems due to the non use of wraps and resultant vacuum drying efficiency. It is believed that shelf life shall be significantly extended and may very well be indefinite.

The apparatus 10 in one preferred form, as shown in FIG. 1, will include a drawer 12 (capable of interlocking in the apparatus when in the closed position) into which a plastic bag B (packaging) containing the item(s) to be processed is/are placed.

A reusable autoclavable carrier in the preferred form of a perforated cage or tray 11 with lid 11a (see FIG. 2) will be inserted into the packaging P. The cage/tray 11 will serve a number of purposes:

act as a carrier tray for the many varied items/loads to be sterilized, facilitate ease of loading and preferably result in uniform or standardized load packaging, enhance the penetration of the sterilant to the items/load due to the perforated design, assist the removal of the sterilant at the end of the sterilization cycle (for steam sterilization reduce the probability of wet-loads), ensure and retain a shape for the packaging at the end of the cycle when the sterile load is subjected to a vacuum and sealed and minimize the probability of the load (sharp items) coming into contact with the packaging, facilitate a uniform shape for ease of stacking for storage and transportation and general handling.

With correct loading of the load/items in the carrier 11 there will potentially be less harm and damage to the load/items during the entire materials handling/logistics cycle e.g. in a hospital environment from the sterile department to theatre and back.

The carrier 11 will preferably be of a form that ensures the packaging P is not damaged by sharp instruments during the whole vacuum sealed life cycle of the sterile load.

When the packaging P is loaded into the drawer 12 of the apparatus 10 it is positioned by location pins 13 which are part of a clamp 14a and sealing anvil 14b and process snorkel arrangement 17 incorporated in the base assembly 16 of the drawer 12a. The packaging P has flaps F with openings O through which are located the location pins 13. The flaps F will be laid over and under the process snorkel 17 (detail A in FIG. 4). Once the packaging P is correctly positioned and the ends thereof are routed over and under the process snorkel 17 the drawer 12 is closed and interlocked in place and the sterilization process can take place.

The invention according to one embodiment is envisaged to accommodate a load containing one cage/tray 11 of half a sterilizing unit [½StU=30 cm×15 cm×60 cm (W×H×L)] per apparatus. This is by way of example and the invention is not limited to this standard size.

The cabinet 18 of apparatus 10 contains a heating plate 20 which preferably forms the base 16 of the drawer 12 when the drawer is closed. In the event that the sterilant is steam the plate will be heated and be the source of the steam supply (the arrangement as shown in the drawings). The combination of the drawer cross-members 19 (see FIG. 5) and the heating plate 20 in the cabinet 18 will ensure that contact is made with the length and breadth of the bottom of the package P.

The heating plate 20 in the cabinet contains, in one form, an electrically heated steam generating element arrangement 21 (see FIG. 5).

A clamp 22a and seal bar 22b arrangement is housed in the cabinet 18 on one side of the cabinet above the drawer opening (see detail B in FIG. 4).

When the drawer 12 is closed, a start instruction is given to a process control unit. The bag/packaging P is detected and the clamp 22a and sealing bar 22b arrangement descends (from the rest position shown in FIG. 4) under control of ram 25, sealing the packaging opening around the intruding snorkel 17 by compressing the packaging and snorkel between the upper clamp 22a and lower clamp 14a. This effectively clamps and seals the packaging about the snorkel 17 as shown in FIG. 3.

At the same time services are connected to the snorkel 17 via vacuum supply socket 23 which mates with socket 23a of snorkel 17 as also shown in FIG. 3.

The drawer 12 is interlocked when the start cycle instruction is given. Vacuum is then applied to remove, via snorkel 17, air from within the packaging and load/items. The cycle pauses to test for vacuum leaks and correct fitment of the packaging and clamp bar arrangement about the snorkel 17. The sterilant is then injected via the snorkel 17 into the packaging P to sterilize the contents.

Should the sterilant be steam, to generate the steam, filtered water is drawn into the internal cavity of the heating plate 20 prior to starting the process via the vacuum pump. Water introduced into this cavity is heated to create the process steam. This steam reservoir provides steam to inside the packaging via the snorkel 17 as directed by the cycle process and additionally acts to directly heat the condensate that has formed within the bottom of the packaging turning it back to steam and reducing the volume requirement for steam into the packaging (effectively recycling the condensate).

A vacuum pump and condensing system (not shown) will provide the vacuum for air and condensate removal under the process control.

A plate 24 is fitted in the cabinet 18 above the packaging P (see FIG. 3) which, after the drawer 12 has been closed, stops the packaging P from blowing to a round shape under pressure. This also maximises contact with the heat plate 20 at the bottom of the cabinet 18. The sides of the packaging will not be completely restrained. The combination of packaging and drawer design will hold the steam pressure within the packaging at the process temperature (usually 134 degrees Celsius).

At the end of the process (steam cycle) a vacuum is pulled on the packaging effectively expelling the steam and the load items will be dried by evaporating the remaining condensate and extracting the remaining vapor.

Once dry, the packaging P is sealed while under vacuum via the seal bar 22b. The upper seal bar 22b contains the sealing element which heat seals the packaging P just behind the clamp 14a, 14b and snorkel 17 by compressing (via further operation of cylinder 25) the seal bar 22b down on to the lower seal anvil 14b. The package is thus sealed following which the seal bar 22b and clamp bar 22a are returned to the raised open position (FIG. 4) and the drawer interlock released. The drawer 12 can thus be opened and the sterilized packaging P is presented for removal. Due to the vacuum sealing it will be immediately obvious if the packaging integrity is intact by visual inspection when a user comes to use the vacuum sealed packaging.

The apparatus capacity is expected to be designed along the capacities consisting of Sterile Units (StU), either in portions or multiples thereof from small dental units to large 'banks' of apparatus with each individual apparatus incorporating all it's services (vacuum, steam) and controller.

It is feasible that a single computer controller could manage a bank of the sterilizing apparatus 10 to replace the traditional multi-load sterilizers in use today. This means that individual items or loads could be prioritized to suit production/user requirements. The potential to incorporate automated loading and unloading systems is also envisaged due to the versatility of the invention.

The bag will need to be made to required specifications and will be specific to this application. In principle it shall be able to withstand temperatures in excess of 134 deg Celsius, and pressure of up to 2 Bar, be resistant to tearing and puncturing and be sealable. It will also be non-porous and be able to hold a vacuum for a prolonged period. Means will be provided to enable the apparatus to either accept an authorized bag and/or detect that it is an authorized bag (e.g. a bar code readable by the apparatus).

The plastic carrier (cage/tray) 11 & 11a will preferably be constructed of homopolymer polypropylene or suitable substitute material or alternatively metal (either aluminum or stainless steel or similar). As disclosed above the carrier 11/11a will contain the items and maintain the packages shape around the carrier under vacuum thereby preventing damage or puncturing of the package's wall integrity from the internal items to be sterilized. The carrier 11/11a may be fitted with an insert or, silicon matting or adjustable/variable clamp/partitioning to best accommodate the items.

It is envisaged that the apparatus 10 may be fitted with a controller incorporating control software that enables real time control of the process parameters irrespective of the load configuration. The benefit of this feature will be that the validation of cycle parameters versus load variability will no longer be a requirement.

The apparatus may be fitted with a printer to print on the packaging or on a label to be attached to the packaging reflecting the cycle parameters and all other relevant data as deemed necessary including in barcode format. This will result in many process, logistic, materials handling, tracking and quality control benefits.

Within the packaging preferably on the carrier 11/11a there will be fixed a clearly visible sterilization monitoring device or indicator to indicate the status of the load and independently confirm whether the items/load is sterile or not. In addition it is envisaged that this will contribute to a sterilized load/items shelf storage life expectancy.

The method and apparatus of the invention provides a revolutionary form of sterilization. The method of sterilization enables the sterilization of items and instruments packaged in a packaging (either plastic bag or similar) with the, combination of the apparatus and packaging effectively forming a sterilizer chamber.

Energy efficiencies can be designed and incorporated to minimize power and sterilant usage while reducing cycle times. Based on the international standard sterile unit sizes, the package is loaded via the drawer type system thereby minimizing operator exposure to the heated areas of the machine. The front loading drawer design allows a seamless integration with modern appliance fitments.

The sterilizer can replace conventional packaging and storage containers and offers extended product shelf life with a substantially quicker processing time. In addition the apparatus does not require an expensive pressure vessel so will be more cost effective to manufacture than conventional sterilizers.

The sterilization medium or sterilant is not limited to steam only as the principles incorporated in the invention can be universally applicable to other mediums currently used in low temperature sterilizers.

The invention as described herein is open to modification as will be appreciated by those skilled in the art. For example, rather than perform as a sterilizer the apparatus could be used as a retort or food cooking apparatus but not limited to only these applications.

A further modification is that rather than vacuum seal the packaging the packaging could be bought back to atmospheric pressure and sealed. Other possibilities are to pressurize or gas flush the packaging and then seal the packaging.

The apparatus shall not be limited to the preferred embodiment and may take the form of a top loader, double ended pass through or auto loading device, or multiples of the apparatus.

Yet a further modification which is envisaged as being within the scope of the invention is to provide a slow release sterilant located within the plastic material of the packaging or the cage itself or alternatively lined on the inside of the plastic packaging or the cage. The intention being that the slow release sterilant would slowly release over time into the interior of the packaging.

Other modifications and improvements to the invention will be apparent to the skilled person and will fall within the scope of the invention as it is intended.

What we claim is:

1. Steam sterilization system including:
   i. an impervious sealable package surrounding a carrier containing item(s) to be sterilized; and
   ii. a steam sterilization apparatus including:
      a. an enclosure to locate and retain a snorkel engageable in an open mouth of the package;
      b. a snorkel clamping unit to seal the open mouth of the package about the snorkel,
      c. a sterilisation unit to selectively apply a vacuum and steam sterilant to the interior of the package to carry out a sterilization process therein; and
      d. a package sealing unit to seal the open mouth of the package at the conclusion of the sterilization process.

2. The system of claim 1 wherein the enclosure is a housing into which the sealable package can be located for the sterilization process to take place, said snorkel opening into the housing.

3. The system of claim 2 wherein the housing is in part formed by a drawer with which the sealable package is engageable, the drawer positionable in a cabinet to assume a closed position and thereby form with the cabinet the housing within which the sealable package is located.

4. The system of claim 3 further including a heating plate which forms the base of the drawer when the drawer is in the closed position.

5. The system apparatus of claim 3 wherein the heating plate is an electronically heated steam generator.

6. The system of claim 3 further including at least one pressure surface contactable with the sealable package to restrain the sealable package during a sterilization process.

7. The system of claim 6 further including a connector for connecting vacuum and sterilant supply to the snorkel when the snorkel sealing unit has sealed the mouth of the packaging on the snorkel.

8. The system of claim 3 wherein the snorkel sealing unit includes a clamp mechanism and a sealing mechanism.

9. The system of claim 3 further including an interlock mechanism to lock the drawer in the closed position.

10. The system of claim 1 wherein the sealable package is non-porous, able to withstand temperatures in excess of 134 deg Celsius and pressure up to 2 bar, be resistant to puncturing or tearing and able to withstand sub-atmospheric pressure for a prolonged period.

11. The system combination of claim 1 wherein the carrier is in the form of a case or tray with perforations.

12. The system of claim 11 wherein the carrier includes a lid.

13. The system of claim 11 wherein the carrier is made from a plastics or metal material.

* * * * *